United States Patent
Dai

(10) Patent No.: US 7,318,908 B1
(45) Date of Patent: *Jan. 15, 2008

(54) INTEGRATED NANOTUBE SENSOR

(75) Inventor: Hongjie Dai, Sunnyvale, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 721 days.

This patent is subject to a terminal disclaimer.

(21) Appl. No.: 10/285,305

(22) Filed: Oct. 31, 2002

Related U.S. Application Data

(60) Provisional application No. 60/335,396, filed on Nov. 1, 2001.

(51) Int. Cl.
- G01N 15/06 (2006.01)
- G01N 33/00 (2006.01)
- G01N 33/48 (2006.01)
- B32B 5/02 (2006.01)
- B32B 27/04 (2006.01)

(52) U.S. Cl. .......................... 422/68.1; 422/50; 422/56; 422/58; 422/62; 422/63; 422/81; 422/82.01; 422/82.02; 422/83; 422/88; 422/98; 422/103; 422/104; 436/43; 436/54; 436/181; 436/149; 73/1.01; 73/1.02; 73/23.2; 73/23.42

(58) Field of Classification Search .............. 422/50, 422/56, 58, 62, 63, 68.1, 81, 82.01, 82.02, 422/83, 88, 98, 103, 104; 436/43, 54, 181, 436/149; 73/1.01, 1.02, 23.2, 23.42
See application file for complete search history.

(56) References Cited

U.S. PATENT DOCUMENTS

| | | | |
|---|---|---|---|
| 4,495,793 A | 1/1985 | Hager | |
| 5,436,167 A | 7/1995 | Robillard | |
| 5,448,906 A | 9/1995 | Cheung | |
| 5,626,650 A | 5/1997 | Rodriguez et al. | |
| 5,653,951 A | 8/1997 | Rodriguez et al. | |
| 5,866,434 A | 2/1999 | Massey et al. | |
| 6,085,576 A * | 7/2000 | Sunshine et al. | .......... 73/29.01 |
| 6,123,819 A * | 9/2000 | Peeters | ....................... 204/452 |
| 6,159,742 A | 12/2000 | Lieber et al. | |

(Continued)

OTHER PUBLICATIONS

Chen, R.J. "Molecular photodesorption from single-walled carbon nanotubes" Applied Physics Letters, Oct. 2001, vol. 79, No. 14, pp. 2258-2260.

(Continued)

Primary Examiner—Brian Sines
(74) Attorney, Agent, or Firm—Crawford Maunu PLLC

(57) ABSTRACT

Integrated nanotube sensors are adapted for detecting various chemical and biological molecules. In one implementation, nanotube sensor arrays are formed as nano-electronic noses capable of such detection, and can be implemented in devices including carbon nanotube-based electronic noses and biochips. Various implementations of the present invention are also directed to nanoscience and nanotechnology applications, such as medical, military and biological applications. In a more particular implementation, nanotubes are produced on full-scale wafers and functionalized. In another more particular implementation, functionalized nanotubes are integrated into addressable devices. With these approaches, various aspects of the present invention have been found to be useful in sensor applications having small size, high density and extreme sensitivity. Such sensor applications are applicable to many aspects of society, and can be implemented for making human lives more safe, secure and healthy.

34 Claims, 6 Drawing Sheets

U.S. PATENT DOCUMENTS

| | | | |
|---|---|---|---|
| 6,162,926 | A | 12/2000 | Murphy et al. |
| 6,400,088 | B1 * | 6/2002 | Livingston et al. ............ 315/94 |
| 6,528,020 | B1 * | 3/2003 | Dai et al. ...................... 422/98 |
| 6,598,459 | B1 * | 7/2003 | Fu ............................. 73/23.34 |
| 6,703,241 | B1 * | 3/2004 | Sunshine et al. .............. 436/8 |
| 6,756,795 | B2 * | 6/2004 | Hunt et al. .................. 324/701 |
| 6,811,957 | B1 * | 11/2004 | Mau et al. ................... 430/315 |
| 6,824,755 | B2 * | 11/2004 | Colbert et al. ........... 423/447.1 |
| 6,824,974 | B2 * | 11/2004 | Pisharody et al. ............. 435/4 |
| 2002/0172963 | A1 * | 11/2002 | Kelley et al. ................... 435/6 |

OTHER PUBLICATIONS

Koshio, A. et al, "In situ laser-furnace TOF mass spectrometry of C36 and the large-scale production by arc-discharge" J Phys. Chem. B, Jul. 2000, vol. 104, pp. 7908-7913, especially pp. 7908-7909.

Jing Kong, Nathan R. Franklin, Chongwu Zhou, Michael G. Chapline, Shu Peng, Kyeongjae Cho, and Hongjie Dai, *Nanotube Molecular Wires as Chemical Sensors*, Science vol. 287, pp. 622-625, www.sciencemag.org, Jan. 28, 2000.

Hongjie Dai, *Integrated Nanotube-Electronic Noses and Bio-Chips (DNA-Chips & Protein Chips)*, pp. 1-7, Aug. 26, 2001.

* cited by examiner

INTEGRATED NANOTUBE SENSOR

RELATED PATENT DOCUMENTS

This is a continuation of U.S. Provisional Patent Application Ser. No. 60/335,306 filed on Nov. 1, 2001 and entitled "Integrated Nanotubes for Electronic Noses," to which priority is claimed under 35 U.S.C. §120 for common subject matter.

FEDERALLY SPONSORED RESEARCH OR DEVELOPMENT

This invention was made with Government support under contract no. N66001-02-1-8911 awarded by the Space and Naval Warfare Systems Center. The Government has certain rights in this invention.

FIELD OF THE INVENTION

The present invention relates generally to carbon nanotubes and more particularly to sensors having carbon nanotubes.

BACKGROUND

Carbon nanotubes are unique carbon-based, molecular structures that exhibit interesting and useful electrical properties. There are two general types of carbon nanotubes, referred to as multi-walled carbon nanotubes (MWNTs) and single-walled carbon nanotubes (SWNTs). SWNTs have a cylindrical sheet-like, one-atom-thick shell of hexagonally-arranged carbon atoms, and MWNTs are typically composed of multiple coaxial cylinders of ever-increasing diameter about a common axis. Thus, SWNTs can be considered to be the structure underlying MWNTs and also carbon nanotube ropes, which are uniquely-arranged arrays of SWNTs.

SWNTs exhibit interesting and useful electrical properties, and may be utilized for a variety of devices, such as integrated molecular electronic devices and others. These devices are applicable to a variety of implementations, such as for sensing chemical and biological species in military missions, defense and protection, environmental monitoring, medical/clinical diagnosis and biotechnology for gene mapping and drug discovery. For instance, detecting chemical weapons in warfare and terrorist attacks are critical to self-alarming and protection. During the Desert Storm conflict, many US soldier were exposed to toxic chemical agents and suffered the Gulf War Syndrome. Other examples include the Tokyo subway poisoning with sarin and the anthrax distribution shortly after the Sep. 11, 2001 terrorist attack in the United States. Advanced chemical sensors are thus highly desired for early and rapid detection and protection in a variety of situations.

Sensors are also important in peaceful environments, such as in medical and biotechnology applications. Useful characteristics of such sensors include the following: (1) fast response, (2) high sensitivity with large response signal of the transducer elements, (3) high selectivity so that the sensor can recognize a specific chemical species, (4) capability of detecting and recognizing as many chemicals as possible, (5) low temperature operation and (6) small, lightweight, compact and convenient to use. Achieving these characteristics, however, has been challenging in previous sensor applications. For example, conventional electrical sensors typically operate at temperatures over 400° C., with a resistance response that is not necessarily significant enough to achieve desired molecular detection. These and other factors have presented challenges for chemical and biological sensing applications.

SUMMARY

The present invention is directed to overcoming the above-mentioned challenges and others related to the types of devices and applications discussed above and in other implementations. The present invention is exemplified in a number of implementations and applications, some of which are summarized below.

According to an example embodiment of the present invention, an integrated sensor including a plurality of carbon nanotubes is adapted for sensing two or more different types of molecular species. The integrated sensor is particularly applicable to molecular sensing applications, such as gas sensing applications, where two or more types of gases are desirably sensed. Moreover, with this approach, difficulties associated with previous approaches to molecular sensing, including those discussed above, are addressed.

In a more particular example embodiment, the integrated sensor discussed above includes first and second carbon nanotubes, each having different compositions and adapted for detecting different molecular species. The compositions of the carbon nanotubes can be tailored for sensing a particular molecular species. In one implementation, one of the nanotubes is functionalized with a substance attached thereto that is adapted for further coupling to molecules for sensing the molecules. In response to the coupling, the carbon nanotube exhibits an electrical response that can be identified as a specific electrical response to the particular molecule being sensed.

In another example embodiment, the integrated sensor discussed above includes detection circuit coupled to electrodes at opposite ends of a carbon nanotube. The detection circuit includes an arrangement for indicating the conductance of the nanotube, with a change in the nanotube's conductance being attributable to the coupling to a molecular species being sensed. Moreover, other aspects, such as a rate of change or amount of change in conductance, can be used for detecting characteristics such as composition and concentration of the molecular species.

According to another example embodiment of the present invention, a system is adapted for sensing molecular species using carbon nanotubes. The system includes an integrated sensor having a plurality of carbon nanotubes, as discussed above, with a sampling arrangement adapted for sampling molecular species and a detection arrangement adapted for detecting the sampled species as a function of an electrical characteristic of one or more of the carbon nanotubes.

In another example embodiment of the present invention, a molecular sensor is manufactured by first growing an array of carbon nanotubes and subsequently functionalizing first and second ones of the carbon nanotubes. The first carbon nanotube is functionalized such that it exhibits strong recognition ability to a first type of molecule, and the second carbon nanotube is functionalized such that it exhibits strong recognition ability to a second type of molecule that is different from the first type of molecule. In one implementation, the functionalization is achieved via an automated pipette system adapted for placing substances in selected locations on a carbon nanotube. With these approaches, functionalization can be implemented for tailoring a molecular sensor for detecting particular molecular species.

In another example embodiment of the present invention, a sensor is fabricated and functionalized for detecting a plurality of molecular species. An array of carbon nanotubes is grown, and first and second ones of the carbon nanotubes are respectively functionalized with first and second species. First and second molecular species are introduced to the array of carbon nanotubes and the first and second carbon nanotubes are used to respectively detect the first and second molecular species.

The above summary of the present invention is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings, in which.

Figure 1A:
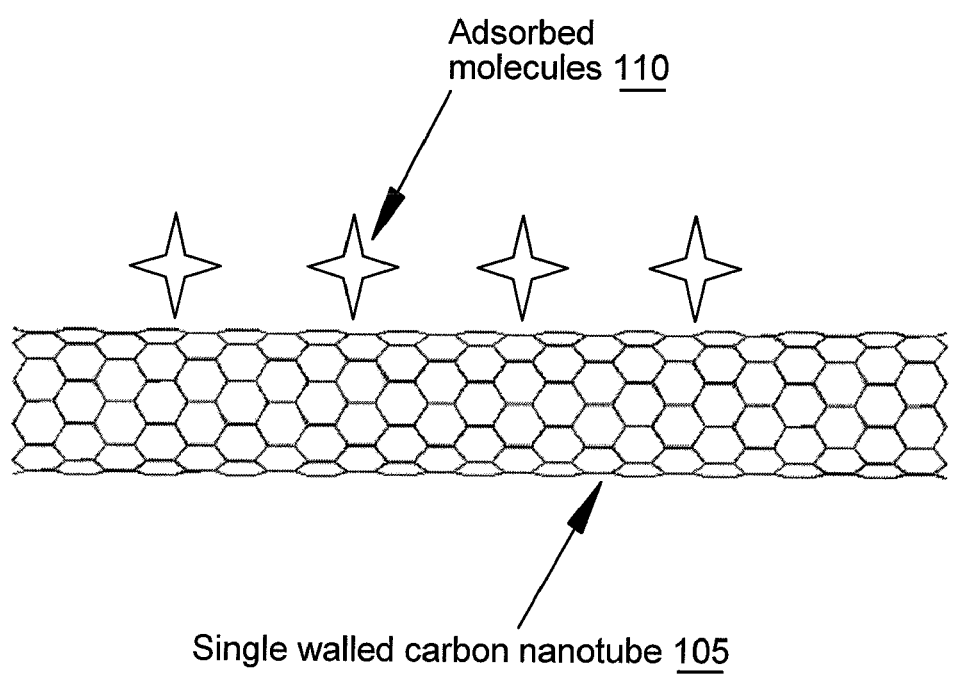
FIG. 1A is a nanotube adapted for detecting molecules, according to an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be applicable to a variety of different types of devices, and the invention has been found to be particularly suited for nanotube sensors and, more particularly, sensors built using carbon nanotubes. While the present invention is not necessarily limited to such applications, various aspects of the invention may be appreciated through a discussion of various examples using this context.

According to an example embodiment of the present invention, integrated nanotube sensors are adapted for detecting various chemical and biological molecules. The nanotube sensors are scaleable, such that large arrays of the sensors can be made in a lab-on-chip fashion. Each nanotube sensor in the array is independently chemically modified to impart functionality and specificity for detecting one or more selected molecules (e.g., gas and/or liquid molecules). In this manner, the array can be used to identify tens, hundreds and even thousands of chemical or biological species at the same time, such as when used as a nanoelectronic nose.

In a more particular example embodiment, a nanotube sensor array includes single carbon nanotubes configured and arranged for detecting small concentrations of gas molecules with high sensitivity at room temperature. Detection schemes using the nanotube sensor are based on chemical interactions between surface atoms of the nanotubes and adsorbed gaseous molecules. The interactions result in a detectable electrical response of the nanotube sensor. More specifically, the electrical response is a function of the type of molecule interacting with the nanotube and, as such, the response is detected and used to identify the type of molecule interacting with the nanotube sensor.

FIG. 1A is a semiconducting SWNT sensor 105 adapted to exhibit a change (increase or decrease) in electrical conductance in response to molecules 110 (e.g., $NO_2$ or $NH_3$) interacting with the sensor 105, according to a more particular example embodiment of the present invention. It has been discovered that charge transfer and/or small changes in the charge-environment of the nanotube can cause drastic changes to its electrical properties, including its conductance. The conductance change results from electron withdrawal (or donation) by molecules 110 adsorbed on the surface of the sensor 105. The change in conductance is detected and used to identify the molecules 110.

The sensor 105 does not necessarily require complex optical or electrochemical accessories and setups, making it readily implemented for detecting a variety of types of molecules in a variety of implementations. In addition, the nanosensors can be integrated as massive arrays of nanosensors having ultra-high densities for analyzing and detecting large numbers of chemicals with high throughput. For more information regarding nanotubes adaptable for implementation in connection with the present invention, reference may be made to Kong et al., Science, 287, 622, 2000, attached hereto as Appendix A and fully incorporated herein by reference.

Figure 1B:
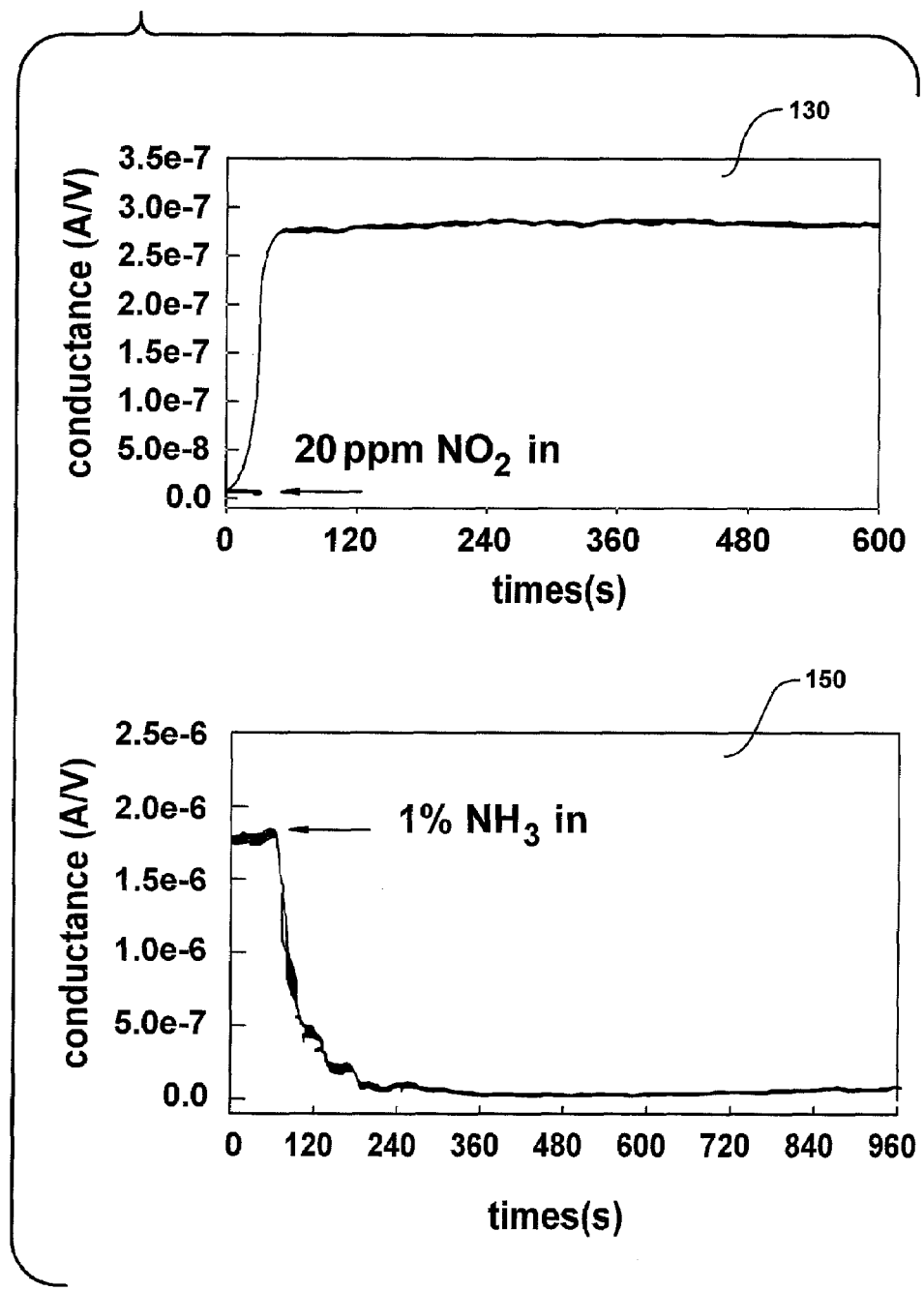
FIG. 1B shows conductance curves of a nanotube electrical sensor for detecting molecules, according to another example embodiment of the present invention.

The response of the nanotube 105 is detected and used to identify a plurality of different types of molecules 110. FIG. 1B shows two curves 130 and 150 showing a change in conductance of the nanotube 105 in response to two such molecules, $NO_2$ and $NH_3$, respectively, used in connection with more particular example embodiments of the present invention. The responses show a change of about 2-3 orders of magnitude in a short time; in some instances the change is exhibited in less than about five minutes, in some other instances, in less than about two minutes and in still other instances, in less than about 1 minute. In this regard, the changes can be used to rapidly detect the presence of the molecules. In each of these instances, the response of the nanotube is recorded (e.g., plotted on a graph) and used as a reference for identifying gas molecules in later tests. For instance, when the response of the nanotube to an unknown gas resembles one of the two curves, the unknown gas is identified as including the molecules relevant to the respective curve detected.

In a more particular implementation, a voltage is applied to the nanotube 105 to cause the nanotube to respond differently to a particular molecular species. For example, the applied voltage can be implemented for causing the nanotube to exhibit a stronger (i.e., more easily detectable) response to a particular molecular species coming in contact with the nanotube 105. The voltage is applied to the nanotube 105 using one or more of a variety of approaches, such as by coupling conductive leads across opposite ends of the nanotube or by applying a gating voltage to the nanotube via a dielectric material. With these approaches, the voltage applied to the nanotube can be used to cause the nanotube to selectively respond to a particular molecular species, or to inhibit a response of the nanotube to a particular molecular species.

Figure 2:
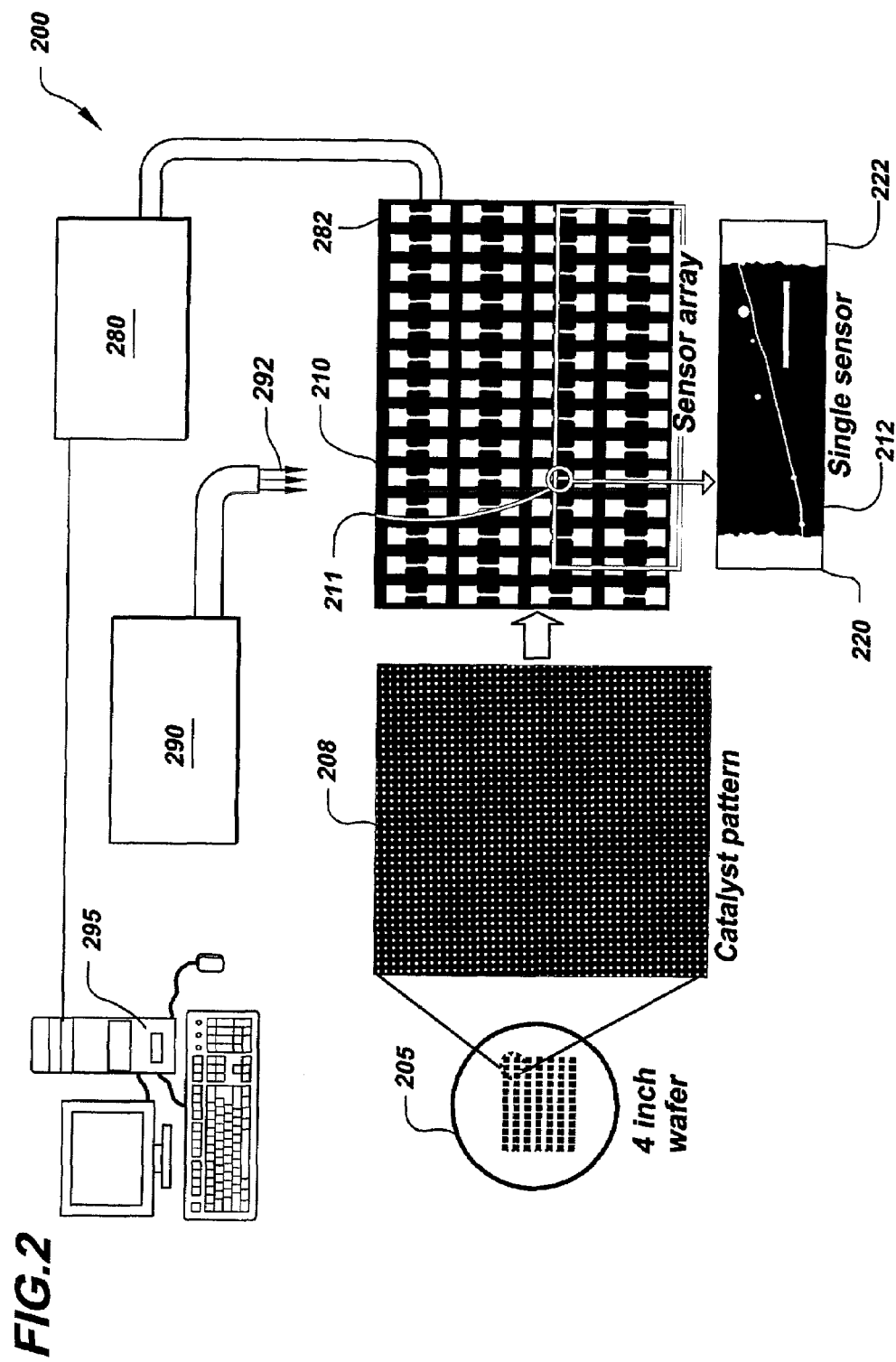
FIG. 2 shows nanotube electronic sensor arrays, according to another example embodiment of the present invention.

FIG. 2 shows a sensing arrangement 200 including arrays of SWNTs formed on a full 4-inch wafer 205 (e.g., a semiconductor chip), according to another example embodiment of the present invention. SWNTs are formed on the wafer 205 using one or more of a variety of approaches. In one instance, catalytic particles (e.g., catalyst islands) are first patterned into regularly spaced arrays 208 on the wafer 205, and nanotubes are grown from the catalytic particles on the wafer using chemical vapor deposition (CVD). Each nanotube is grown extending between two catalyst particles, as shown in portion 210 of the pattern 208. By predefining the locations of the catalyst particles, the nanotubes are defined in well-defined locations, which is particularly useful for mass production of nanotube devices. In this instance, individual nanotube sensor 211 includes a carbon nanotube 212 extending between two electrodes 220 and 222, respectively, with each electrode being located at a catalyst particle location. The electrodes may, for example, include titanium or other conductive material formed over the catalyst particles. Each of the nanotubes is then chemically modified to exhibit a selected response to one or more molecules, and the array is used for detecting such molecules, as discussed above.

The sensor arrays are fabricated using one or more readily-available semiconductor processing techniques, such as photolithography, metal deposition and liftoff, and can be implemented with a variety of types of electrical circuitry. In one implementation, the electrodes are wire bonded to a test circuit for electrical sensing measurements, and the test circuit is adapted to detect changes in electrical characteristics of the nanotubes. The nanotube sensors on the chip are functionalized, for example, by treatment with a selected species, such as by doping, chemically coupling or otherwise associating the selected species with the carbon nanotube, such as discussed below.

The functionalization imparts selectivity and specificity to each nanotube sensor (nano-sensor), and the nanotube sensors can be functionalized differently from each other, for example, for configuring the functionalized nanotubes to exhibit specific sensing characteristics. In one implementation, one or more of the nanotube devices are functionalized so that each nanotube exhibits strong recognition ability to a different specific type of molecule (e.g., such that the response of the nanotube is readily detectable). The collective responses of all of the nano-sensors on the chip are detected and used to give a definitive identification of one or more chemical species in the environment in which the nanotube is present. With this approach, a variety of types of species can be detected, such as in a gas comprising a plurality of types of molecules. In addition, by using characteristics such as the strength of a particular detected response and the number of sensors detecting a particular species, the concentration of a particular species in a gas can be detected.

For more information regarding wafer-scale implementations to which the present invention is applicable (e.g., for growing nanotubes for sensor applications), reference may be made to U.S. Provisional Patent Application Ser. No. 60/335,396, filed on November 1, 2001 and entitled "Patterned Growth of Single-walled Carbon Nanotubes on Wafers" and to U.S. patent application Ser. No. 10/285,311, filed concurrently herewith and now U.S. Pat. No. 7,183,228 entitled "Carbon Nanotube Growth," both of which are fully incorporated herein by reference.

The functionalization of the nanotubes discussed above is performed in a variety of manners using one or more of a variety of chemical species, depending upon the application. For example, one or more of a variety of metal species can be placed onto the nanotubes. In one particular implementation, palladium metal is chemically attached to a nanotube such that the palladium-functionalized nanotube is responsive to molecular $H_2$ in the atmosphere to which it is exposed. The chemistry between $H_2$ and Pd (see, e.g., Kong et al. Adv. Mater., in press) changes an electrical characteristic of the nanotube, and a response of the nanotube related to the changed characteristic is detected and used to identify $H_2$ in the atmosphere.

In another example embodiment, a detection circuit 280 is coupled across one or more of the carbon nanotubes in the array 208, with the detection circuit being coupled across one carbon nanotube sensor 282 in FIG. 2 by way of example. The detection circuit 280 is adapted for detecting a change in one or more of the nanotubes in the array 208, with the change being used, as discussed above, for sensing. A direct or indirect readout from the nanotube sensor 282 is provided for detecting the change. In one implementation, the detection circuit 280 includes a computer programmed for identifying a detected change (response) of the nanotube sensor 282 as an indication of a particular species contacting the nanotube sensor. For instance, using stored responses of the nanotube sensor 282 to particular known molecular species, the computer is programmed to compare a detected response to the stored responses and, upon finding a match, identifying the response as corresponding to a particular molecular species.

In another example embodiment, a user interface 295, such as a touchpad, computer or other input device, is coupled to the detection circuit 280 and adapted for communicating with the detection circuit. In one implementation, the user-interface 295 is adapted for providing programming inputs to the detection circuit 280. In another implementation, the user interface 295 provides an indication of the presence of a particular molecular species as detected by the detection circuit, for example, by displaying a graphical response.

In another example embodiment, a sampling arrangement 290 is adapted for sampling a molecular species and introducing the sampled species to the array 208 (as shown by arrows 292). In one implementation, the array and sampling arrangement are included in a portable gas sensor, with the sampling arrangement gathering gas from the environment in which the portable gas sensor is located. Using a fan and/or natural currents to intake gas, the sampling arrangement is adapted for gathering a sample of the gas from the intake and providing the sample to the array 208. In another implementation, the sampling arrangement 290 is arranged for gathering gas from an environment where the array 208 is not located and for transporting the gathered gas to the array. For instance, when sampling gas from a manufacturing process or as products of combustion (e.g., an automobile engine), the sampling arrangement 290 gathers gas and delivers the gathered gas to a location where the array 208 is located.

In another implementation, a flushing arrangement is adapted for flushing (i.e., removing and/or desorbing) species from the array 208. For example, by using the sampling arrangement 290 to introduce an inert gas to the array 208, molecular species are flushed from the array. In addition, a variety of other approaches for flushing, such as those involving controlling the environment around the array 208, applying heat to the array and others are implemented in various instances.

In another example embodiment, some or all of the sensing arrangement 200 is adapted for transportation in a transportation arrangement, such as a carrying case and/or a vehicle. In one implementation, the transportation arrangement is adapted for transporting the sensing arrangement 200 (or portions thereof) into an environment using remote control. With this approach, toxic environments can be entered and sampled without necessarily human involvement.

Figure 3:
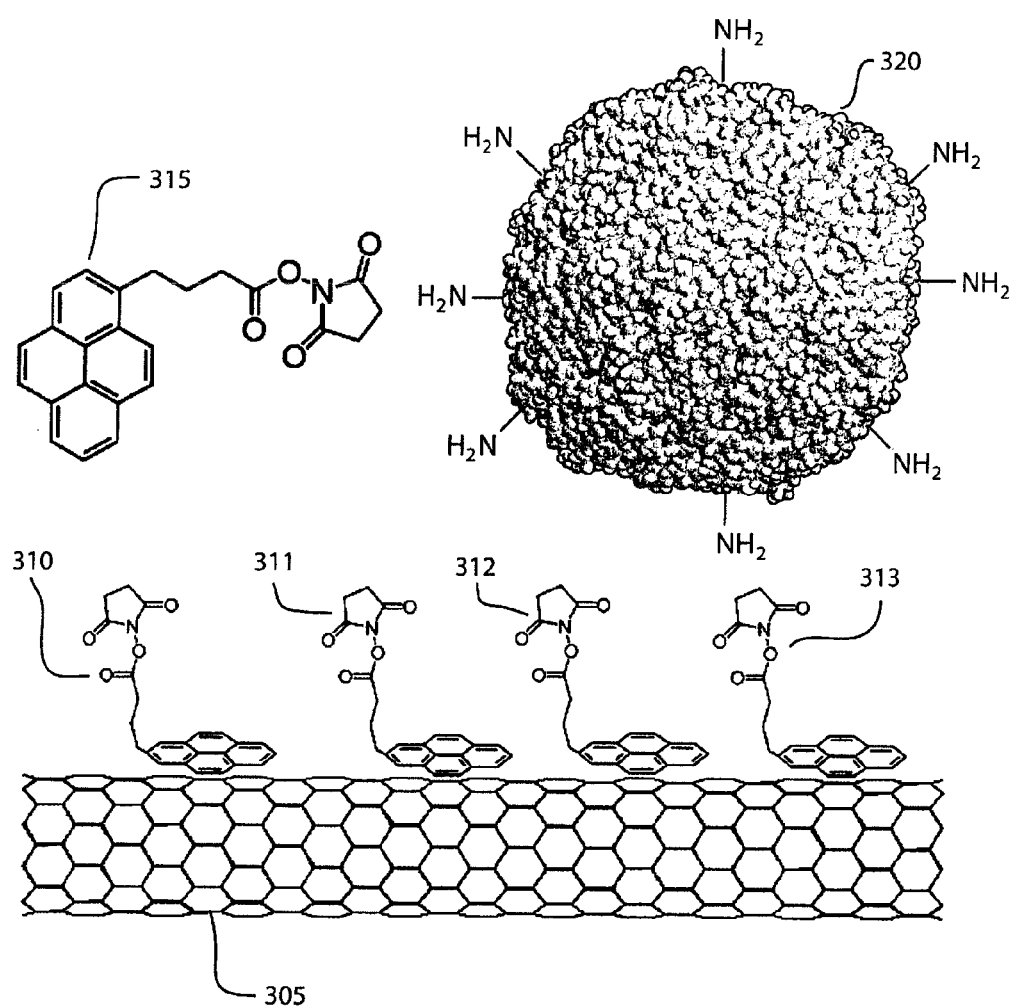
FIG. 3 shows non-covalent functionalization, adaptable for use in connection with another example embodiment of the present invention.

FIG. 3 shows planar molecules π-stacked onto sidewalls of a nanotube and adapted to non-covalently functionalize a nanotube, according to another example embodiment of the present invention. This planar-stacked approach shown in FIG. 3 may, for example, be used in connection with one or more of the example embodiments discussed herein, such as those shown and described in connection with FIG. 2. The chemical groups on the planar molecules are used to covalently link to and immobilize a variety of chemical or biological species. More specifically, planar molecules 310, 311, 312 and 313 are irreversibly adsorbed onto a nanotube 305 (see, e.g., Chen et al., J. Am. Chem. Soc. 123, 3838, 2001). The adsorbed planar molecules are adapted to covalently link to a biomolecule, such as molecule 320. By so doing, the nanotubes can be functionalized with a variety of proteins, enzymes, antigens, antibodies and nucleic acid oligomers. In addition, irreversible adsorption can be used to non-covalently functionalize the nanotube with linear polymers, dendrimers and porphyrins compounds (see, e.g., Shim et al., submitted to J. Am. Chem. Soc.).

In another example embodiment of the present invention, a sensor arrangement including an array of functionalized nanotube sensors, such as the sensors discussed herein, is adapted for detecting and identifying multiple gaseous species in an environment. Potential gases to be identified include $O_2$, $H_2$, CO, $NO_2$, NO, $NH_3$, $H_2S$ and $H_2O_2$. The sensor arrangement is adapted to use a response of the functionalized nanotubes to specific gaseous species, as well as related mechanisms behind electrical property changes of the functionalized nanotubes, to detect one or more molecules in the environment as a function of the response. For example, when a functionalized nanotube is known to exhibit a particular electrical characteristic in the presence of a specific gaseous species, the detection of that particular electrical characteristic can be used to identify that the specific gaseous species is present.

The functionalized nanotubes in the sensor arrangement respond in a variety of manners, depending upon the functionalization used. In one implementation, a charge transfer upon direct adsorption of a molecule to a nanotube sensor is the dominant mechanism that affects the nanotube characteristics. In another implementation, dipole effects are a dominant mechanism used for sensing molecules in the environment. Using these and other mechanisms, the sensor arrangement can be adapted to respond strongly to a particular type of gas and not to others (e.g., a relatively larger charge transfer and/or a relatively higher dipole effect). This is particularly useful for identifying a presence of a particular type of gas.

The nanotube sensors of the present invention are useful for detecting a variety of molecules, including toxic chemicals in military and defense applications. In one implementation, a nanosensor is adapted for sensing nerve agents including the organophosphate compound sarin. In this implementation, the nanotube sensor is functionalized with catalysts for sarin hydrolysis, such as metal ions and their complexes ($Cu^{+2}$, $ZrO^{+2}$, $MoO2^{+2}$) or iodobenzoic acid derivatives. The catalysts facilitate (i.e., catalyse) a hydrolysis reaction. The rapid sarin hydrolysis reaction on the nanotube surface changes an electrical characteristic of the nanotube and the change in electrical characteristic is used to detect the presence of sarin.

In another example embodiment of the present invention, one or more of a variety of organic molecules and polymers are placed onto carbon nanotubes, and a wide range of biological molecules are subsequently anchored onto the nanotubes. The nanotubes are thus bio-functionalized and form a nanotube bio-chip. The biological molecules may include, for example, proteins, enzymes, antigens, antibodies, nucleic acids and oligomers. The bio-functionalized nanotubes, combined with their electrical sensitivity to surface events, make nanotubes ideal nano-biosensors.

Figure 4:
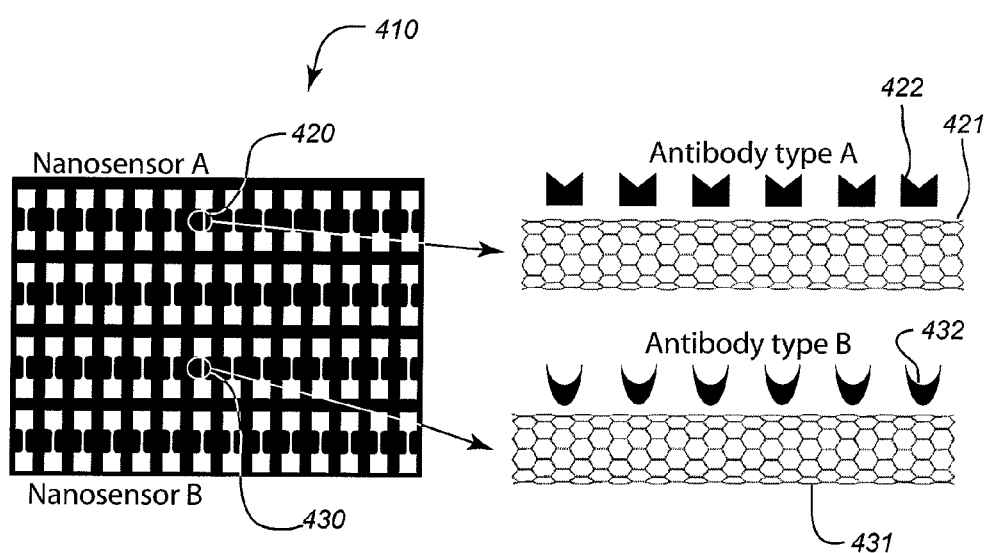
FIG. 4 shows micro-plotting for functionalization of nanosensors, according to another example embodiment of the present invention.

FIG. 4 shows a nanotube electronic bio-chip 410, according to a particular example embodiment of the present invention. The bio-chip includes first and second nanosensors 420 and 430, each nanosensor functionalized with a specific molecule. The first and second nanosensors include carbon nanotubes 421 and 431, respectively. Carbon nanotube 421 is functionalized with antibody A 422 and carbon nanotube 431 is functionalized with antibody B 432. Antibody A has a different recognition property than antibody B, such that each antibody is adapted to react differently to molecules, relative to one another. In this manner, the single bio-chip is adapted for sensing two types of species using different antibodies. Furthermore, by adding other antibodies to other ones of the nanotube sensors on the chip 410, a multitude of biological species can be detected.

The bio-functionalized nanotubes in FIG. 4 are adaptable for use in a variety of applications. In one particular example embodiment, nanosensor arrays are functionalized with oligomers and proteins to form a nanotube chips (nano-bio-chip) that is sensitive to DNA and proteins. The chip includes nanotube electrical sensors with each nanotube sensor being functionalized by different oligomers or antibodies. Upon specific binding of a complementary oligomer or antigen to the functionalized nanotube sensor, molecular recognition events give rise to large sensor responses due to change in the charge environment of the nanotube. This response is detected and used to recognize the change in charge environment and thereby detect the presence of the complementary oligomer or antigen. In this manner, the nanotube based DNA and protein (or antibody) chips are useful for rapid screening of a multitude of oligomers and proteins.

These nano-biochips exhibit a variety of advantages, including advantages over previously used systems, such as optical detection systems. For example, the nano-biochips can be made fluorescence-label free, are adaptable for achieving direct electrical readout without relying on complex optical systems, and in DNA and protein detection applications, exhibit greater than 100 times higher density than optical chips. In the latter example, high throughput of DNA chips and protein chips is facilitated as many more types of molecules can be screened with each chip, relative to the types that can be scanned with an optical chip. In addition, the nanotube biochips are directly relevant to a multitude of implementations, including military and defense situations. For instance, functionalizing the chip with antibodies directed against Australia Group listed agents facilitates specific recognition of many of these agents in a rapid and high throughput fashion (the Australia Group is an informal group of countries that are committed to combating the proliferation of chemical and biological weapons).

Figure 5:
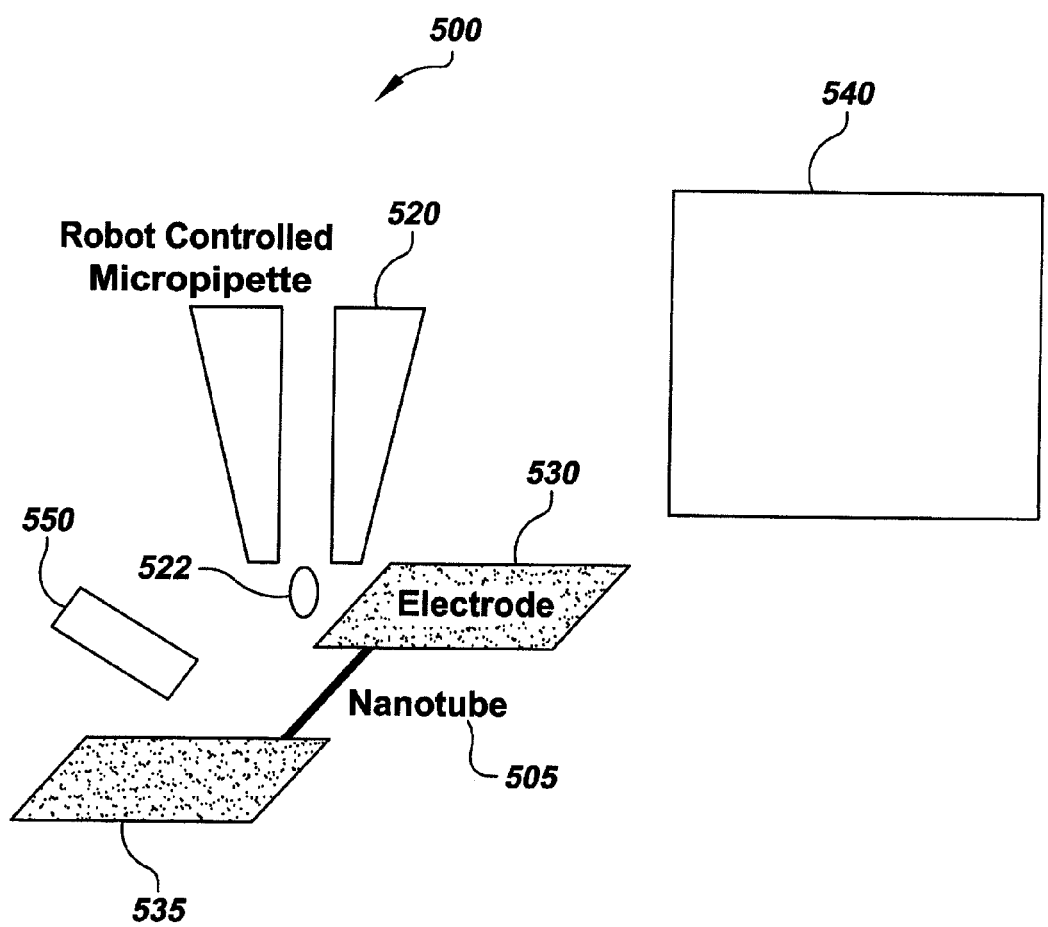
FIG. 5 is a nanotube electronic bio-chip, according to another example embodiment of the present invention.

The nanotubes can be functionalized using a variety of systems and methods. FIG. 5 illustrates one example system 500 in which one or more nanotube sensors are functionalized using spatially defined sensor-specific functionalization with a micro-plotting approach, according to another example embodiment of the present invention. The micro-plotting approach may, for example, include techniques typically used for making DNA and protein chips. A micropipette 520 (e.g., robotically-controlled) is used to place a tiny chemical droplet 522 onto a sensor having a nanotube 505 between electrodes 530 and 535. The placement of the droplet is effected in a manner similar to dip-pen lithography, and can be used to apply droplets of different chemicals to an array of nanotube sensors, thereby imparting different functionalities to each of the sensors in the array. Chemicals that can be used to functionalize the nanotube sensors include metal salt solutions that can be converted into metal or metal oxides later. In addition, various ligands, proteins, DNA, polymers, dendrimers and porphyrins can be placed onto nanotubes in a controlled fashion.

In one implementation, the system 500 includes a chamber 540 adapted for growing the nanotube 505. The chamber 540 may, for example, be similar to a conventional CVD chamber and adapted for introducing a carbon-containing gas to a catalyst in the chamber at an elevated temperature, and for reacting the carbon-containing gas for growing the carbon nanotube. The catalyst may, for instance, be patterned on a wafer as discussed above in connection with FIG. 2.

In another implementation, the system 500 includes a doping arrangement 550 adapted for doping a species, such as Boron, to the carbon nanotube 505. In one instance, the doping arrangement 550 includes an ion implantation arrangement adapted to implant the species to the nanotube 505. In another instance, the doping arrangement 550 is adapted to introduce a species to the nanotube 505 for doping the nanotube (e.g., using heat and/or other mechanisms).

The example embodiments discussed herein are applicable to a variety of implementations. For instance, the sensor applications herein may be applied to molecular sensors for industrial, military, law enforcement and home use, such as for airport security, drug traffic control, environmental monitoring, land mine detection, food inspection and laboratory analysis. In addition, for more information regarding such implementations, reference may be made to the attached Appendix B, which is fully incorporated herein by reference.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. For instance, such changes may include modifying the carbon nanotubes such that they exhibit a response to a particular molecular species, which is useful, for example, for tailoring the nanotubes for applications involving sensing the particular molecular species. Other changes may include using other types of nanotubes, such as those including Boron or Nitrogen, or substituting multi-walled nanotubes for single-walled nanotubes. Such modifications and changes do not depart from the true spirit and scope of the present invention.

What is claimed is:

1. A molecular sensor comprising a plurality of carbon nanotubes including:
   a first carbon nanotube having a first composition and adapted for detecting a first molecular species; and
   a second carbon nanotube having a second composition and adapted for detecting a second molecular species, the first composition being different from the second composition.

2. The molecular sensor of claim 1, wherein the first and second carbon nanotubes have different functional molecular species respectively coupled thereto.

3. The molecular sensor of claim 2, wherein one of the functional molecular species includes at least one of: a metal; a biological species; a protein, an enzyme, anantigen, an antibody and a nucleic acid oligomer.

4. The molecular sensor of claim 2, wherein at least one of the first and second carbon nanotubes is adapted to electrically respond to a molecular species being introduced thereto.

5. The molecular sensor of claim 4, wherein at least one of the first and second carbon nanotubes is adapted to respond to at least one of: DNA, proteins and oligomers.

6. The molecular sensor of claim 4, wherein the at least one of the first and second carbon nanotubes is adapted to change conductance in response to the molecular species.

7. The molecular sensor of claim 2, wherein at least one of the first and second carbon nanotubes includes a functional molecular species that is adapted to bind to a complementary molecular species.

8. The molecular sensor of claim 7, wherein a carbon nanotube having the functional molecular species to which the complementary molecular species is bound is adapted to exhibit a different charge environment in response to the binding of the complementary molecular species.

9. The molecular sensor of claim 2, wherein at least one of the functional molecular species includes a catalyst adapted to facilitate a chemical reaction that includes coupling a molecular species to the respective carbon nanotube to which the functional species is attached.

10. The molecular sensor of claim 1, wherein the first carbon nanotube is adapted to exhibit a stronger electrical response to the first molecular species, relative to an electrical response exhibited by the first carbon nanotube to a molecular species that is different than the first molecular species.

11. The molecular sensor of claim 1, wherein at least one of the carbon nanotubes includes a molecular species covalently bonded thereto.

12. The molecular sensor of claim 1, wherein at least one of the carbon nanotubes includes a stacked planar molecule having a chemical group covalently linked to a molecular species.

13. The molecular sensor of claim 1, wherein at least one of the carbon nanotubes includes an irreversibly adsorbed molecule.

14. The molecular sensor of claim 13, wherein the irreversibly adsorbed molecule includes at least one of a linear polymer, a dendrimer and a porphyrins compound.

15. The molecular sensor of claim 1, wherein at least one of the first and second nanotubes is adapted to detect a molecular species at room temperature.

16. The molecular sensor of claim 1, wherein at least one of the first and second nanotubes is adapted to respond differently to a molecular species in response to a voltage being applied to the at least one nanotube.

17. The molecular sensor of claim 16, wherein the at least one nanotube is adapted to selectively respond to different molecular species in response to the voltage being applied thereto.

18. A molecular sensor comprising:
an array of electrodes on a chip; and
a plurality of carbon nanotubes, each carbon nanotube extending between two of the electrodes and having a functional species attached thereto, at least two of the carbon nanotubes having different functional species and being adapted to respond differently to molecular species, wherein the chip is configured and arranged for electrically coupling across each carbon nanotube via the electrodes for detecting at least two different molecular species via the response of the carbon nanotubes.

19. The molecular sensor of claim 18, wherein each electrode has exactly one carbon nanotube extending therefrom.

20. The molecular sensor of claim 18, wherein each electrode comprises a catalyst particle and wherein each carbon nanotube extends between two of the catalyst particles.

21. The molecular sensor of claim 20, wherein the catalyst particles are adapted to facilitate the growth of the carbon nanotubes.

22. The molecular sensor of claim 18, wherein the chip is configured and arranged for wire bonding to a test fixture adapted for detecting an electrical characteristic of each carbon nanotube.

23. The molecular sensor of claim 18, further comprising a detection circuit electrically coupled to the array of electrodes and adapted to use an electrical response of the nanotubes to detect the presence of at least one molecular species.

24. The molecular sensor of claim 23, wherein the detection circuit is programmed to identify the detected electrical response as a response that indicates the presence of the at least one molecular species.

25. The molecular sensor of claim 23, wherein the carbon nanotubes are adapted to respond differently, relative to one another, to gasses in a gas mixture and wherein the detection circuit is adapted to detect the composition of the gas mixture from the different responses of the carbon nanotubes.

26. The molecular sensor of claim 23, wherein the detection circuit is adapted to use the detected response to detect a concentration of the at least one molecular species.

27. The molecular sensor of claim 23, wherein the detection circuit is adapted to use an electrical response of the nanotubes over time to detect the presence of the at least one molecular species.

28. The molecular sensor of claim 23, wherein the detection circuit is adapted to provide a direct electrical readout from the nanotubes.

29. A system for sensing a plurality of molecular species, the system comprising:
a molecular sensor having a plurality of carbon nanotubes, at least two of the carbon nanotubes being differently functionalized and adapted to respond differently to different molecular species;
a sampling arrangement adapted to sample a molecular species and to introduce the sample to the molecular sensor; and
a detection circuit electrically coupled to the molecular sensor and adapted to detect an electrical response of the sensor to the sample and programmed to use the detected response to detect the presence of at least one molecular species in the sample.

30. The system of claim 29, further comprising a user interface adapted to provide a user output that indicates the presence of the at least one molecular species.

31. The system of claim 29, further comprising a transportation arrangement adapted to transport the sampling arrangement to a selected area for sampling.

32. The system of claim 31, further comprising a remote control arrangement adapted for controlling the transportation arrangement.

33. The system of claim 29, further comprising a flushing arrangement adapted to flush the molecular species from the molecular sensor.

34. The system of claim 29, wherein the sampling arrangement is adapted for sampling exhaust from a combustion engine.

* * * * *

UNITED STATES PATENT AND TRADEMARK OFFICE
CERTIFICATE OF CORRECTION

PATENT NO.          : 7,318,908 B1
APPLICATION NO.     : 10/285305
DATED               : January 15, 2008
INVENTOR(S)         : Hongjie Dai Page 1 of 1

It is certified that error appears in the above-identified patent and that said Letters Patent is hereby corrected as shown below:

In the Claims

Col. 10, line 18, Claim 3: "anantigen" should read --an antigen--.

Signed and Sealed this

Fourteenth Day of April, 2009

JOHN DOLL
*Acting Director of the United States Patent and Trademark Office*